(12) United States Patent
Jasra et al.

(10) Patent No.: US 7,087,791 B2
(45) Date of Patent: Aug. 8, 2006

(54) CATALYSED ACYLATION OF ALKYLATED BENZENE DERIVATIVES

(75) Inventors: Raksh Vir Jasra, Gujarat (IN); Beena Tyagi, Gujarat (IN); Yogiraj Mansukhlal Badheka, Gujarat (IN)

(73) Assignee: Council of Scientific and Industrial Reasearch, New Delhi (IN)

( * ) Notice: Subject to any disclaimer, the term of this patent is extended or adjusted under 35 U.S.C. 154(b) by 0 days.

(21) Appl. No.: 10/678,902

(22) Filed: Oct. 2, 2003

(65) Prior Publication Data

US 2005/0171385 A1 Aug. 4, 2005

(51) Int. Cl.
*C07C 45/00* (2006.01)

(52) U.S. Cl. .................. 568/314; 568/316; 568/335

(58) Field of Classification Search .......... 568/314, 568/316, 335
See application file for complete search history.

(56) References Cited

U.S. PATENT DOCUMENTS

| | | | | |
|---|---|---|---|---|
| 5,068,448 A | * | 11/1991 | Lindley et al. | 568/319 |
| 5,395,975 A | * | 3/1995 | Siegel et al. | 568/316 |
| 6,194,616 B1 | * | 2/2001 | Spagnol et al. | 568/322 |
| 6,384,285 B1 | * | 5/2002 | Choudary et al. | 568/319 |

* cited by examiner

*Primary Examiner*—Johann Richter
*Assistant Examiner*—Sikarl A. Witherspoon
(74) *Attorney, Agent, or Firm*—Rutan & Tucker, LLP

(57) ABSTRACT

An ecofriendly process for acylation of an alkylated benzene derivative has increased selectively towards para position and comprises a step of reacting the alkylated benzene derivative with an acylating agent in the presence of nitrobenzene, dichlorobenze, dimethylsulfolane, and/or benzotrile, and a crystalline alumino silicate catalyst having general formula $M_{2/n}O.Al_2O_3.xSiO_2.wH_2O$, wherein M is an alkali cation, a rare earth cation, and/or a proton, wherein the Si/Al ratio is in the range of 5.5 to 20, wherein the step of reacting is performed at temperature between 80° to 140° C. for 5 to 25 hours. In a further step, the solid catalyst is separated from the reaction mixture of step, and in yet another step, the acylated alkyl benzene derivative is separated from the mixture.

13 Claims, No Drawings

CATALYSED ACYLATION OF ALKYLATED BENZENE DERIVATIVES

FIELD OF THE INVENTION

The present invention relates to an eco-friendly process for catalysed acylation of alkylated benzene derivatives preferably in the para position. More particularly, the present invention relates to zeolite catalysed acylation of isobutylbenzene for the preparation of acylated aromatic compound, namely p-isobutylactophenone.

BACKGROUND AND PRIOR ART DESCRIPTION

Acylated aromatic compound is chiefly used in pharmaceutical industries. Analgesics (painkillers) are a very well known group of drugs that include asprerine, acetaminophen [Tylenol] and ibuprofen [Motrin, Advil and Medipren]. In addition of their analgesic properties, ibuprofen and asprerine are members of non-steroidal anti-inflammatory group of drugs and are thus used to reduce swelling and inflammation. Ibuprofen was introduced as a carboxylic acid in 1969, to help provide relief of rheumatoid arthritis. It is believed to be gentler on stomach than aspirin. It metabolites rapidly by the body, usually leaving the body via urination within 24 hours of intake. Ibuprofen is a main component for Advil®, Bayer®, Midol 200®, Motrin IB® and Nuprin®. It is used for the treatment of inflammation and pain caused by rheumatoid arthritis and osteoarrthritis, as well as soft tissue injuries, such as tendentious and bursitis. It is also used for the rapid relief of fever and in mild to moderate pain, such as menstrual cramps.

The industrial process for manufacturing of ibuprofen starts with the acylation of isobutylbenzene in the presence of conventional Friedel-Crafts catalysts, described as under.

(A) Boots Process

Boots company of England in 1960 developed a process, which is covered in U.S. Pat. No. 3,385,886, having six steps for the production of ibuprofen. It starts with the acylation of isobutylbenzene in the presence of $AlCl_3$ by using acetic anhydride as an acylating agent. This multi step process results in large quantity of unwanted waste chemical as by products. Much of the waste that is generated as a results of many atoms of the reactant not being incorporated into the desired products (Ibuprofen) but into by-products. Consequently, process has poor atom economy/atom utilisation.

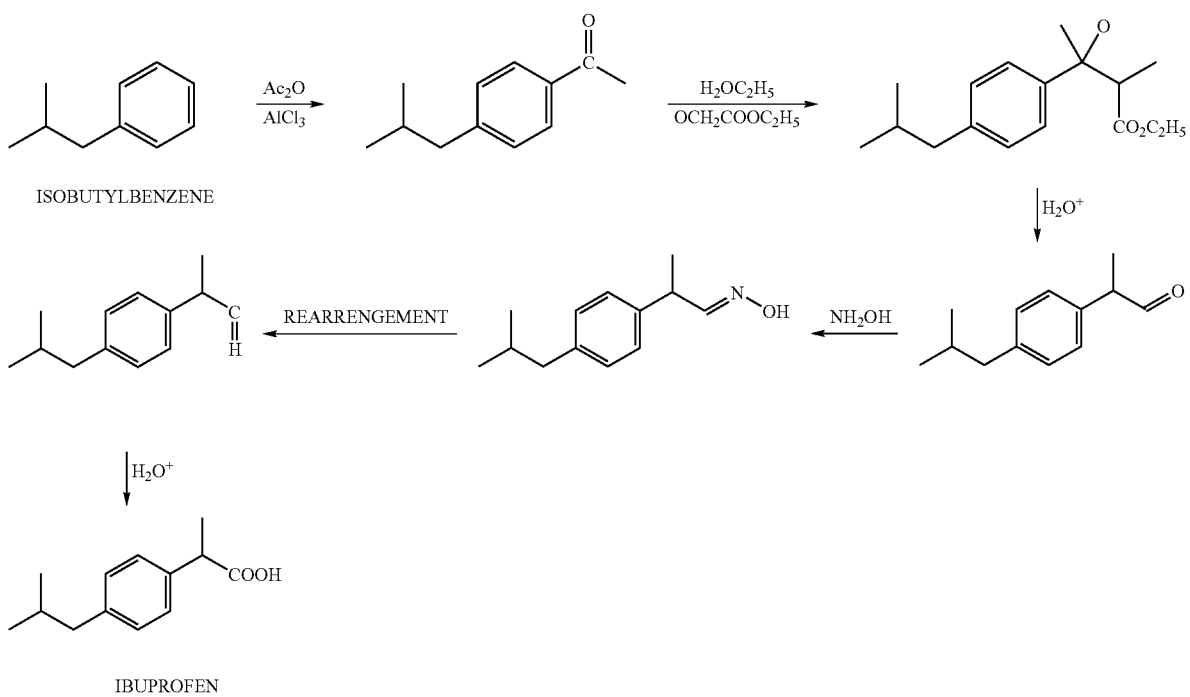

ISOBUTYLBENZENE

IBUPROFEN (B) Hoescht Process.

It is a three-step synthesis of ibuprofen, which is taught in U.S. Pat. Nos. 4,981,995 and 5,068,448. The Hoescht process also starts with the acylation of isobutylbenzene in the presence of HF by using acetic anhydride as an acylation agent. Compared to Boots process, hoescht process is more eco-friendly, but still the utilisation of hazardous HF for acylation is not safe from handling point of view.

Chemical equation:

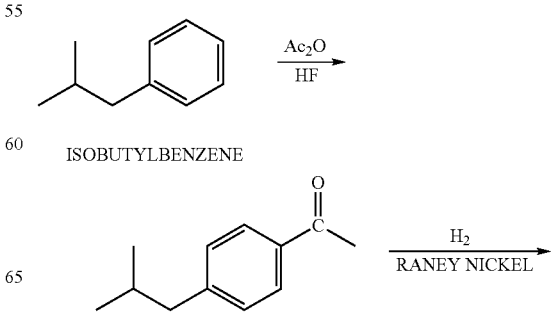

ISOBUTYLBENZENE

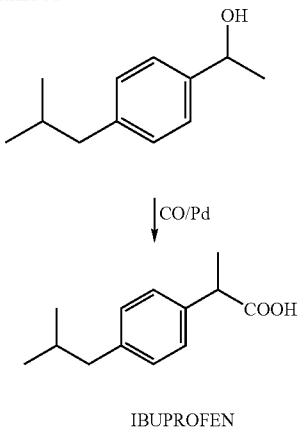

IBUPROFEN

Research efforts to find eco-friendly and safer catalysts, which can replace $AlCl_3$ and HF, have been directed in the literature and are reviewed here.

Reference is made to the work of E. Nandanan., et al., Indian J. of Chemistry, Vol-37B, December 1998, pp-1221–1227, wherein the preparation of 4-acyl isobutylbenzene using $AlCl_3$ and acetyl chloride as an acylating agent is taught. Nandanan et al. used dichloromethane as a solvent. This process has disadvantages of the separation of the catalyst and non-regenerability of the catalyst as well as long reaction time, which is not industrially feasible.

Reference is made to the work of P Andy, et al., J. of Catalysis-192, 215–223 (2000), wherein the Beta zeolite based acylation of isobutylbenzene using acetic anhydride as an acylating agent is taught. This process has disadvantage of low conversion (12% after 20 hours) and it is not economical to commercialize.

Reference is made to the work of Bich Chichi, et al., J. of Mol. Cat.-42 (1987)-229–235, wherein the Friedel-Craft acylation of aromatic compound (BTX) with carboxylic acid over cation exchanged montmorillonite is taught. This process has disadvantage of poor selectivity towards the para position during the acylation of toluene.

Reference is made to the work of C. De Castro, et al., J. of Mol. Cat.-A:Chemical-134 (1998) 215–222, wherein the acylation of xylene is reported using crotonic acid as an acylating agent in the presence of heteropoly acid and large pore zeolite. This process has disadvantages like, in some case, significant amount of alkylation also occurs leading to generation of undesired by-products and loss of starting compound.

Reference is made to the work of AJ. A. van der Weerdt in his personnel communication wherein the acylation of toluene by isobutyryl chloride in the presence of $AlCl_3$. This process has disadvantages like more than stochiometric amounts of aluminum chloride is used due to complexation with the ketone, need to have a post reaction effluent treatment process and use of corrosive and irritant $AlCl_3$. The major drawback of the above stated process is separation of catalysts after completion of the reaction. This necessitates a long, expensive treatment following hydrolysis, extraction of the organic phase, separation of organic and aqueous phase and even drying of latter. Further, there are problems with aqueous saline effluent which has to be neutralised and which necessities additional operation. The Lewis acid cannot be recycled, as it has been hydrolysed.

Reference is made to the work of I. Akhrem, et al., J. Chem Soc. Comm. P. 257, Vol-3, February 1993, wherein the acylation of benzene is reported by acetyl bromide employing $Al_2Br_6$ as catalyst to p-tertiary butylacetophenone. This process having disadvantages of waste generation and non-recoverable catalysts as well as requirement of catalysts/reagents which is more than stochiometric amount.

Reference is made to the work of Y. Izumi, et al., Chem. Lett.-P. 1987, 1992 Vol-B 10, wherein the acylation of p-xylene by using benzoyl chloride/anhydride is done in the presence of heteropoly acid. This process has disadvantage like, occurrence of simultaneous alkylation in the presence of heteropoly acid, which leads to generation of undesired by-product.

Reference is made to the work of Lapierre R. B, et al., U.S. Pat. No. 4,899,008, February 1990, wherein the alkylation of benzene and toluene with C2 to C4 alkanes over acidic zeolites is reported. Benzene was reacted with $C_3H_8$ over H-ZSM-5 at 385–399° C./6184 kPa for 49 hours to give MePh, 9.92%. This process having disadvantage of operation at very high temperature and pressure.

Reference is made to the work of Klein, Alfons, Fiege et al., Ger. Off. D. E. 3839853, 31 May 1990, wherein the alkylation of p-Cresol with cyclohexanol or cyclohexene is done in the presence of acidic zeolite. This process has the disadvantages of operation at high temperature and pressure and low conversions.

Reference is made to the work of Davydov, D. V, et al., Izv. Akad. Nauk, SSSR, Ser Khim, 1990 (3), 708–710 (RUSS), wherein $LnCl_3$ (Ln=Pr, Dy, Er, Sm, Yb) and $Yb(O_3SCF_3)$ are used as a catalyst for the electrophilic acylation of benzene and toluene with acylchloride and benzaldehyde. This process has disadvantages of multi-step reaction and non-regeneration of the catalyst.

Reference is made to the work of Nakatani, Jinro, kamoto et al., Jp: 09, 278705 wherein benzene is acylated with $CH_3CH_2COOH$ in the presence of zeolite-beta at 270° C. to give about 10% of propiophenone. This process has disadvantages of high temperature and very long reaction time which discourages commercial utilization of the process.

Reference is made to the work of Choudary, et al., (India).Jpn. Kokai Tokkyo Koho Jp 2001278833 A2 10 Oct. 2001, 16 pp, wherein the acylation of isobutylbenzene is done using acetic anhydride as an acylating agent in the presence of nanocrystalline zeolite. This process has the disadvantages of utilizing nanosized materials, which makes the whole process more costly. Wt. % conversion of isobutylbenzene was only 30 wt. %.

Reference is made to the work of Eun Joo Jang, Kyung et al., J. of Molecular Catalysis A, 138(1999)-25-36, wherein they have reported regioselective synthesis of ibuprofen via palladium complexes. In this process, ibuprofen is synthesised by hydrocarbonylation of 1-(4-isobutylyphenyl) ethanol with carbon monoxide and water. This process has disadvantage of the utilisation of carbon monoxide gas, which is hazardous, and very difficult to handle; furthermore, in this process, 4-isobutylacetophenoe is produced by conventional Friedel-Craft acylation of isobutylbenzene.

Reference is made to the work of Botella, P, et al., J. Catal., 195(1),161–168 (English)2000, Wherein the acylation of toluene was carried out with acetic anhydride over beta zeolite in a stainless-steel autoclave at 150° C. by keeping arene/anhydride ratio of 10 to 20. This process is having disadvantages of high temperature and also the need of a large amount of acetic anhydride, which will needed to be separated from the product and unused toluene.

Reference is also made to the Assignee's earlier U.S. Pat. No. 6,384,285 titled "Process for the preparation of 4'-isobutylacetophenone" which is incorporated herein as reference. The aforesaid U.S. Patent teaches a process for the preparation of 4'-isobutylacetophenone from isobutylbenzene which comprises reacting isobutylbenzene with acetic anhydride as an acylating agent in the presence of a zeolite beta catalyst at a temperature ranges between 60 to 165 degree. C. for 2–12 h separating the catalyst by filtration from the reaction mixture and recovering the product by a conventional method. The Inventors would like to mention here that the aforesaid U.S. Patent does not teach use of a solvent during the process of acylation of isobutylbenzene using aceticanhydride. The Inventors have surprisingly found that use of some specific solvents during the process of acylation increases the percentage conversion and also the selectivity towards para position. The Applicants have also found that not all solvents are able to increase the percentage conversion and the selectivity. For example, when solvents such as cyclohexane, dichloroethane, dichloromethane and nitromethane are added during the process of acylation, the conversion does not take place. In view of the above, it is submitted that the nature of the solvent added during the process of acylation is very critical. The success of a particular solvent in increasing the percentage conversion and the selectivity cannot be determined merely by extrapolation and it needs lot of research and intellectual input. Hence, the present invention should not be considered as being obvious over the U.S. Pat. No. 6,384,285.

OBJECTS OF THE PRESENT INVENTION

The main object of the present invention is to provide an eco-friendly process for acylation of alkylated benzene derivatives preferably at para position in presence of a solvent, which obviates the drawbacks as detailed above.

Another object of the process is to provide a process wherein crystalline aluminosilicate based solid acid heterogeneous catalysts, which are environmentally friendly and safe in handling are used for acylation of alkylated benzene derivatives.

Still another object of the present invention is to develop crystalline aluminosilicate catalysts based acylation process for alkylated aromatic compounds, which operates at moderate conditions of temperature and pressure and yields high conversions with selectivity towards para acylated product being more than 90%.

Yet another object of the present invention is to provide a process wherein acylating agent does not generate any hazardous by-product.

Yet another object of the present invention is to provide a process wherein the solvent added can be easily separated from the products or reactants.

Another object of the present invention is to provide a process wherein acylation of alkylated aromatic compound is carried out catalytically with high atom utilisation and low mass ratio of waste to desired product.

DETAILED DESCRIPTION OF THE PRESENT INVENTION

An ecofriendly process for acylation of alkylated benzene derivatives preferably in the para position, said process comprising the steps of:
(a) reacting the alkylated benzene derivatives with an acylating agent such as chloride or anhydride of carboxylic acid or its homologues essentially and selectively in the presence of a solvent selected from the group consisting of nitrobenzene, dichlorobenzene, dimethylsulfolane, benzonitrile or mixtures thereof and a crystalline alumino silicate catalyst having general formula:

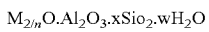

wherein,
M is an alkali and/or rare earth cation or proton,
Si/Al ratio is in the range of 5.5 to 20, and
the weight percentage of alkali and/or lanthanide cation is in the range of 10 to 30;
at temperature in the range of 80° to 140° C. for a time period in the range of 5 to 25 hours;
(b) separating the solid catalyst from the reaction mixture of step (a), and
(c) separating the acylated alkyl benzene derivatives from the mixture of step (b).

In an embodiment of the present invention, the alkylated benzene derivative is isobutylbenzene.

In another embodiment of the present invention, the acylated alkyl benzene derivative is isobutylacetophenone.

In yet another embodiment of the present invention, the acylated alkyl benzene derivative is preferably p-isobutylacetophenone.

In still another embodiment of the present invention, the crystalline alumino-silicate catalyst used is selected from zeolite-Y and Zeolite-β.

In one more embodiment of the present invention, the crystalline alumino-silicate catalyst is preferably modified using rare earth cations.

In one another embodiment of the present invention, the crystalline alumino-silicate catalyst is modified using lanthanum and/or cerium in the range of 10 to 30% by weight.

In a further embodiment of the present invention, the acylating agent is preferably acetic anhydride.

In a furthermore embodiment of the present invention wherein in step (a), the alkylated benzene derivatives are reacted with acylating agent at atmospheric conditions.

In an embodiment of the present invention wherein in step (a), the alkylated benzene derivatives are reacted with acylating agent at temperature in the range of 100° to 140° C. and preferably at temperature in the range of 100° to 120° C.

In another embodiment of the present invention, the solid catalyst separated in step (b) is regenerated for re-use.

In still another embodiment of the present invention, the reaction is generally carried out at is atmospheric pressure. Autogeneous pressure is used when the temperature of the reaction is more than the boiling points of the reactants and/or products.

In a typical procedure for the preparation of the catalyst, crystalline alumino-silicates namely zeolite-Y, Beta, ZSM-5 or mordenite in its sodium form was taken and further treated in following two steps a) conversion to H-form and b) conversion of H-from to lanthanides form.

For preparing H-form of the zeolite, 10 grams of sodium zeolite was refluxed with 100 ml of 1M NH4Cl solution for 6 hours at 80 to 100° C. The system was cooled following which the solid catalyst was filtered, washed with hot distilled water till the filtrate became chloride free as tested by AgNO3 and dried in a laboratory oven overnight at 110° C. for removing of the moisture. Thus dried sample was calcined at 550° C. for 6–10 hours to get H form of zeolite. The catalyst thus obtained was cooled and ambient temperature.

In a typical procedure for the preparation of final zeolite catalysts in lanthanide form, 10 grams of the above prepared zeolite in its H-form was refluxed with 100 ml of 0.01 M solution of soluble salt like nitrate, chloride, or acetate of relative lanthanide cations for 6 to 10 hours at 80 to 100° C. Then the catalyst was filtered after cooling the contents, washed with hot distilled water till the filtrate became anion free and dried in a laboratory oven overnight at 110° C. for removing of the moisture. Activation of these prepared catalysts was done at 400° C. in air for 4 to 10 hours prior to catalytic studies.

Analysis of above catalysts were done by X-ray diffraction using Philips MPD system, and BET surface area using Micromeritics ASAP-2010 which clearly indicate the preservation of crystallinity during modification of the catalysts.

Catalytic studies using above catalysts were done in a continuous stirred tank reactor (CSTR) of 50 ml capacity equipped with temperature controller, water circulator, magnetic stirrer and moisture trap. Typically, isobutylbenzene and acetic anhydride in the molecular ratio ranging from 1:1 to 1:3 were taken in a 50 ml capacity round bottom flask to which the activated catalyst was added so as the ratio of isobutylbenzene/catalysts is ranging from 2 to 10. The activation of the catalysts was done at 400° C. for 4 hours. The round bottom flask was fitted with a condenser through which constant temperature water was circulated. Moisture trap was attached at the end of the condenser. The contents of the flask were constantly stirred using a magnetic stirrer. The flask was kept in an oil bath whose temperature was slowly raised to desired reaction temperature. The content of the flask were analysed at different time intervals ranging from 5 to 25 hours by Gas Chromatography, HP model 6890, using capillary column HP-5. Percent conversion of isobutylbenzene was calculated using following equation Percent conversion=$[no-nf/no] \times 100$ Where, no=Number of moles of alkylated aromatic compound introduced before reaction.

nf=Number of moles of alkylated aromatic compound remaining in the reaction mixture after reaction.

In the present invention crystalline alumino-silicate based catalysts are developed for the acylation of isobutylbenzene to produce selectively p-acylated product. Among all these catalysts studied rare earth modified zeolite Beta showed highest activity followed by H-Y, Clays and Mordenite. It is also observed that more polar solvent like nitrobenzene, o-dichlorobenzene and dimethylsulfolane helps to proceed reaction in the forward direction resulting to higher conversion of isobutylbenzene, while non-polar solvent like cyclohexane, hexane are showing less activity. Moreover, low boiling point solvent like dichloromethane and dichloroethane are not practically utilisable because of solvent vapour loss. It is also observed that isobutylbenzene over acetic anhydride ratio also affect the conversion. The inventive steps in the present work includes, 1. The use of highly selective solvents for increasing the percentage conversion and the selectivity of the acylation is novel and non-obvious. It should be noticed here that the use of the solvents may increase as well as decrease the percentage conversion and the selectivity and only after much trial and error it can be determined which particular solvent will increase the percentage conversion of acylation and the selectivity towards para position.
2. Simple modification of crystalline alumino-silicates with rare earth cations in the range of 10 to 30 weight percent to introduce surface acidity which make the catalysts more suited for acylation reactions leading to higher conversion and para position selectivity.
3. The acylation reaction is carried out in single step and separation of the catalysts from the reaction mixture can be easily done by filtration.
4. The lower temperature and pressure conditions which favour the selectivity for para position, which is desired.
5. The catalytic reaction proceeds at relatively moderate temperature of 120° C. and at atmospheric pressure, which makes the process energy efficient.
6. Catalysts can be regenerated with a simple process and reused.

The following examples are given by the way of illustrations and therefore should not be constructed to limit the scope of the present invention.

EXAMPLE-1

10 gm of crystalline alumino-silicate namely zeolite-Beta in sodium form was refluxed with 100 ml of 1M aqueous solution of ammonium chloride for 6 hours at 80° C. This was followed by filtration, washing with hot distilled water till the filtrate become chloride free as checked by silver nitrate solution. Thus obtained solid was dried overnight as 110° C. The dried sample was calcined at 550° C. in air for removing ammonia and calcined solid was termed as H-Beta. 0.5 gm of thus prepared catalyst was preactivated [400° C. in muffle furnace for 4 hrs.] and mixed with 10 milimoles of acetic anhydride and 10 milimoles of isobutylbenzene with 10 ml of nitrobenzene in a 50 ml of two necked round bottom flask. This round bottom flask was then put in an oil bath equipped with temperature controller, magnetic stirrer, condenser and circulator. The temperature of the oil bath was then slowly raised to the desired one, i.e., to 100° C. The sample were taken out periodically by means of syringe and analysed by gas chromatography using HP-5 column. The percent conversion of isobutylbenzene was 6.35% with 95% selectivity after 20 hours as shown in table-1.

EXAMPLE-2

0.5 gm of crystalline alumino-silicate namely zeolite-Y was preactivated [400° C. in muffle furnace for 4 hrs.] and mixed with 10 milimoles with acetic anhydride and 10 milimoles of isobutylbenzene with 10 ml of nitrobenzene in a 50 ml of two necked round bottom flask. This round bottom flask was then put in an oil bath equipped with temperature controller magnetic stirrer, condenser and circulator. The temperature of the oil bath was then slowly raised to the desired one i.e. to 100° C. The sample were taken out periodically by means of syringe and analysed by gas chromatography using HP-5 column. The percent conversion of isobutylbenzene was 1.38% with 97% selectivity after 20 hours as shown in table-1.

EXAMPLE-3

10 gm of crystalline alumino-silicate namely zeolite Na-ZSM-5 was refluxed with 100 ml of 1M aqueous solution of ammonium chloride for 6 hrs. at 80° C. This was followed by filtration, washing with hot distilled water till the filtrate become chloride free as checked by silver nitrate solution. Thus obtained solid was dried overnight as 110° C. The dried sample was calcined at 550° C. in air for removing ammonia and calcined solid was termed as H-ZSM-5 zeolite. 0.5 gm of thus prepared zeolite catalysts was preactivated [400° C. in muffle furnace for 4 hrs.] and mixed with 10 milimoles with acetic-anhydride and 10 milimoles of isobutylbenzene with 10 ml of nitrobenzene in a 50 ml of two necked round bottom flask. This round bottom flask was then put in an oil bath equipped with temperature controller magnetic stirrer, condenser and circulator. The temperature of the oil bath was then slowly raised to 100° C. The samples were taken out periodically by means of syringe and analysed by gas chromatography using HP-5column The percent conversion of isobutylbenzene was nil even after 20 hours as shown in table-1.

EXAMPLE-4

10 gm of crystalline alumino-silicate namely zeolite Na-Mordenite was refluxed with 100 ml of 1M aqueous solution of ammonium chloride for 6 hours at 80° C. This was followed by filtration, washing with hot distilled water till the filtrate become chloride free as checked by silver nitrate solution. Thus obtained solid was dried overnight at 110° C. The dried sample was calcined at 550° C. in air for removing ammonia and calcined solid was termed as H-Mordenite zeolite. 0.5 gm of thus prepared zeolite catalysts was preactivated [400° C. in muffle furnace for 4 hrs.] and mixed with 10 milimoles with acetic-anhydride and 10 milimoles of isobutylbenzene with 10 ml of nitrobenzene in a 50 ml of two necked round bottom flask. This round bottom flask was then put in an oil bath equipped with temperature controller magnetic stirrer, condenser and circulator. The temperature of the oil bath was then slowly raised to the desired one, i.e., to 100° C. The sample were taken out periodically by means of syringe and analysed by gas chromatography using HP-5 column. The percent conversion of isobutylbenzene was nil even after 20 hours as shown in table-1.

EXAMPLE-5

L0 gms of alumino-silicate namely raw montmorrilonite clay was mixed with 10 litres of distilled water and stirred for 24 hours. It was allowed to settle down for 24 hours and then supernant was decant and then clay dried in natural sun light to get upgraded clay in its sodium form. It was then treated with 2NH2SO4 for 6 hours, filtered and washed with hot distilled water to make it free from sulphate as checked with the solution of silver nitrate. 0.5 gm of thus prepared H-Montmorrilonte was mixed with 20 milimoles with acetic-anhydride and 10 milimoles of isobutylbenzene with 10 ml of nitrobenzene in a 50 ml of two necked round bottom flask with preactivated [120° C. in oven for 12 hrs]. This round bottom flask was then put in an oil bath equipped with temperature controller magnetic stirrer, condenser and circulator. The temperature of the oil bath was then slowly raised to the desired one, i.e., to 120° C. The sample were taken out periodically by means of syringe and analysed by gas chromatography using HP-5 column. The percent conversion of isobutylbenzene was nil even after 20 hours as shown in table-1.

EXAMPLE-6

10 gm of crystalline alumino-silicate namely zeolite-Y was refluxed with 100 ml of 0.01M solution of cerium nitrate at 80° C. for 6 hours, followed by filtration and washing with hot distilled water to make it free from nitrate as checked by silver nitrate. The resultant solid was dried at 110° C. for overnight and calcined at 550° C. to get Ce—Y zeolite.

10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts as prepared above. This round bottom flask was then put in an oil bath equipped with temperature controller, magnetic stirrer, and condenser and water circulator. The temperature of the oil bath was then slowly raised to the desired one, i.e., to 100° C. The sample were taken out periodically by means of syringe and analysed by gas chromatography using HP-5 column. The percent conversion of isobutylbenzene was 2.08% with 98% selectivity after 20 hours as shown in table-1.

EXAMPLE-7

10 gm of crystalline alumino-silicate namely zeolite Beta as prepared in Example-1 was refluxed with 100 ml of 0.01M solution of cerium nitrate at 80° C. for six hours, followed by filtration and washing with hot distilled water to make it free from nitrate as checked by silver nitrate. The resultant solid was dried at 110° C. for overnight and calcined at 550° C. to get Ce-Beta, 10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts as prepared above. This round bottom flask was then put in an oil bath equipped with temperature controller, magnetic stirrer, condenser and water circulator. The temperature of the oil bath was then slowly raised to the desired one i.e. 100° C. The sample were taken out periodically by means of syringe and analysed by gas chromatography using HP-5column. The percent conversion of isobutylbenzene was 11.27% with 95% selectivity after 20 hours as shown in table-1.

EXAMPLE-8

10 gm of crystalline alumino-silicate zeolite Y was refluxed with 100 of 0.01M solution of lanthanum nitrate at 80° C. for six hours, followed by filtration and washing with hot distilled water to make it free from nitrate as checked by silver nitrate. The resultant solid was dried at 110° C. for overnight and calcined at 550° C. to get La—Y zeolite. 10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts as prepared above. This round bottom flask was then put in an oil bath equipped with temperature controller, magnetic stirrer, condenser and water circulator. The temperature of the oil bath was then slowly raised to the desired one i.e. 100° C. The sample were taken out periodically by means of syringe and analysed by gas chromatography using HP-5 column. The percent conversion of isobutylbenzene was 2% with 94% selectivity after 20 hours as shown in table-1.

EXAMPLE-9

10 milimoles of isobutylbenzene, 10 milimoles of acetic anhydride and 10 ml of nitrobenzene were mixed in a 50 ml of two necked round bottom flask with 0.5 gm of preactivated [400° C. in muffle furnace for 4 hrs] catalyst Ce-Beta, as prepared in Example-7. This round bottom flask was then put in an oil bath equipped with temperature controller, magnetic stirrer, condenser and water circulator. The temperature of the oil bath was then slowly raised to the desired one i.e. to 100° C. The sample were taken out periodically by means of syringe and analysed by gas chromatography using HP-5 column. The percent conversion of isobutylbenzene was ranging from 6 to 15% with selectivity from 92 to 98% in the time interval of 5 to 25 hours as shown in table-2.

EXAMPLE-10

10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts Ce-Beta, as prepared in Example-7. This round bottom flask was then put in an oil bath equipped with temperature controller, magnetic stirrer, condenser and water circulator. The temperature of the oil bath was then slowly raised to the desired one i.e. to 120° C. The sample were taken out periodically by means of syringe and analysed by gas chromatography using HP-5 column. The percent conversion of isobutylbenzene was ranging from 8 to 20% with selectivity from 89 to 100% in the time interval of 5 to 25 hours as shown in table-2.

EXAMPLE-11

10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller, magnetic stirrer, condenser and water circulator. The temperature of the oil bath was then slowly raised to the desired one, i.e., to 140° C. The sample were taken out periodically by means of syringe and analysed by gas chromatography using HP-5 column. The percent conversion of isobutylbenzene was ranging from 7.5 to 9.15% with selectivity from 85 to 100% in the time interval of 5 to 25 hours as shown in table-2.

EXAMPLE-12

10 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 8.5 to 12.8% with selectivity from 95 to 97% in the time interval of 10 to 20 hours as shown in table-2.

EXAMPLE-13

20 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 34 to 36% with selectivity from 60 to 92% in the time interval of 10 to 20 hours as shown in table-2.

EXAMPLE-14

30 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 12 to 16% with selectivity from 72 to 81% in the time interval of 10 to 20 hours as shown in table-2.

EXAMPLE-15

20 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalysts, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 34 to 36% with selectivity from 89 to 92% in the time interval of 10 to 15 hours as shown in table-2.

EXAMPLE-16

20 milimoles of acetic anhydride, 10 milimoles of isobutylbenzene and 5 ml of nitrobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., 120° C. The sample were taken out periodically by means of syringe and analysed by gas chromatography using HP-5 column. The percent conversion of isobutylbenzene was ranging from 13 to 14% with selectivity from 77 to S5% in the time interval of 10 to 20 hours as shown in table-2.

EXAMPLE-17

20 milimoles of acetic anhydride, 10 milimoles of isobutylbenzene and 10 ml of nitrobenzene were mixed in a 50 ml of two necked round bottom flask with 0.1 gm of preactivated [400° C. in muffle furnace for 4 hrs] catalysts, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 8 to 20% with selectivity from 88 to 94% in the time interval of 5 to 10 hours as shown in table-2.

EXAMPLE-18

20 milimoles of acetic anhydride, 10 milimoles of isobutylbenzene and 10 ml of nitrobenzene were mixed in a 50 ml of two necked round bottom flask with 0.15 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 9 to 19% with selectivity from 88 to 95% in the time interval of 5 to 10 hours as shown in table-2.

EXAMPLE-19

20 milimoles of acetic anhydride, 10 milimoles of isobutylbenzene and 10 ml of nitrobenzene were mixed in a 50 ml of two necked round bottom flask with 0.25 gm of preactivated [400° C. in muffle furnace for 4 hrs] catalyst, Ce-Beta, as prepared in example-7. This round bottom flask was then put in an oil bath equipped with temperature controller magnetic stirrer condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 5 to 13% with almost 100% selectivity in the time interval of 10 to 20 hours as shown in table-2.

EXAMPLE-20

20 milimoles of acetic anhydride, 10 milimoles of isobutylbenzene and 10 ml of nitrobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 10 to 27 to 34% with selectivity from 87 to 89% in the time interval of 5 to 10 hours as shown in table-2.

EXAMPLE-21

200 milimoles of acetic anhydride, 100 milimoles of isobutylbenzene and 100 ml of nitrobenzene were mixed in a 250 ml of two necked round bottom flask with 5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 24 to 31% in with selectivity from 87 to 95% the time interval of 5 to 10 hours as shown in table-2.

EXAMPLE-22

After the reaction described in Example 19, The solid portion was separated by filtration, washing with acetone till the filtrate became colourless. Thus washed sample was put in oven for overnight at 110° C. and then activated at 400° C. for 4 hours in a muffle furnace in air prior to use. Thus activated catalysts was mixed with 20 milimoles of acetic anhydride, 10 milimoles of isobutylbenzene and 10 ml of nitrobenzene were mixed in a 50 ml of two necked round bottom flask. This round bottom flask was then put in an oil bath equipped with temperature controller, magnetic stirrer, condenser and water circulator. The temperature of the oil bath was then slowly raised to the desired one, i.e., to 120° C. The sample were taken out periodically by means of syringe and analysed by gas chromatography using HP-5 column. The same process was repeated for further four times and the percent conversion of isobutylbenzene was 37, 36, 22, 8, and 5% with selectivity from 81, 81, 90, 96 and 96% after 15 hours reactionj time in first, second, third and forth regeneration respectively as shown in table-2.

EXAMPLE-23

The catalysts obtained after first regeneration process as described in Example-21 was activated at 500° C. for 4 hours prior to use. Thus activated catalysts was mixed with 20 milimoles of acetic anhydride, 10 milimoles of isobutylbenzene and 10 ml of nitrobenzene were mixed in a 50 ml of two necked round bottom flask. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 22 to 30% with selectivity from 83 to 87% in the time interval of 10 to 15 hours as shown in table-3.

EXAMPLE-24

20.0 milimoles of acetic anhydride, 10.0 milimoles of isobutylbenzene and 10.0 ml of nitrobenzene were mixed in a 50 ml of Parr autoclave with 0.5 gm of preactivated [400° C. in muffle furnace for 4 hrs] catalyst, Ce-Beta, as prepared in Example-7. This auto clave is equipped with temperature controller magnetic stirrer, condenser and water circulator. The temperature of the reaction vessel was then slowly raised to the desired one, i.e., to 120° C. After 8 hours of reaction time the autoclave was cooled down and the reaction mixture was analysed by gas chromatography using HP-5 column. The percent conversion of isobutyl benzene was 27% with 90% selectivity after 8 hours reaction time as shown in table-3.

EXAMPLE-25

20 milimoles of acetic anhydride and 10 milimoles of isobutylbenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator, from the top of the condenser nitrogen gas was slowly passed during the reaction. The temperature of the oil bath was then slowly raised to the desired one, i.e., to 120° C. The sample were taken out periodically by means of syringe and analysed by gas chromatography using HP-5 column. The percent conversion of isobutylbenzene was 9.87% with 88% selectivity after 10 hrs reaction time as shown in table-3.

EXAMPLE-26

20 milimoles of acetic anhydride and 10 milimoles of isobutylbenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator, from the top of the condenser argon was slowly passed during the reaction. The temperature of the oil bath was then slowly raised to the desired one, i.e., to 120° C. The sample were taken out periodically by means of syringe and analysed by gas chromatography using HP-5 column. The percent conversion of isobutylbenzene was 3% with 87% selectivity after 10 hours reaction time as shown in table-3.

EXAMPLE-27

30 milimoles of acetic anhydride, 10 milimoles of isobutylbenzene mixed in a 50 ml of two necked round bottom flask with 0.5 gm of preactivated [400° C. in muffle furnace for 4 hrs] catalyst, Ce-Beta, as prepared in example-7. This round bottom flask was then put in an oil bath equipped with temperature controller, magnetic stirrer, spiral condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 3 to 6% with 40 to 46% selectivity in the time interval of 10 to 15 hours as shown in table-3.

EXAMPLE-28

60 milimoles of acetic anhydride, 10 milimoles of isobutylbenzene mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, spiral condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was ranging from 6 to 8% with 24 to 40% selectivity in the time interval of 10 to 15 hours as shown in table-3.

EXAMPLE-29

20 milimoles of acetic anhydride, 10 milimoles of isobutylbenzene and 10 ml of Dimethylsulfolane were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was 20% with 82% selectivity after 15 hours as shown in table-4.

EXAMPLE-30

20 milimoles of acetic anhydride, 10 milimoles of isobutylbenzene and 10 ml of Benzonitrile were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was 5.6% with 100% selectivity after 8 hours as shown in table-4.

EXAMPLE-31

20 milimoles of acetic anhydride, 10 milimoles of isobutylbenzene and 10 , of nitrobenzene were mixed in a 50 ml of two necked round bottom flask with 0.5 gm of preactivated [400° C. in muffle furnace for 4 hrs] catalyst, Ce-Beta. as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was 37% with 92% selectivity after 15 hours as shown in table-4.

EXAMPLE-32

20 milimoles of acetic anhydride, 10 milimoles of isobutylbenzene and 10 ml of dichlorobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e. to 120° C. The sample were taken out periodically by means of syringe and analysed by gas chromatography using HP-5 column. The percent conversion of isobutylbenzene was 29% with 88% selectivity after 15 hours as shown in table-4.

EXAMPLE-33

20 milimoles of acetic anhydride, 10 milimoles of isobutylbenzene and 10 ml of acetic anhydride were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e. to 120° C. The sample were taken out periodically by means of syringe and analysed by gas chromatography using HP-5 column. The percent conversion of isobutylbenzene was 6.6% with 24% selectivity after 15 hours as shown in table-4.

EXAMPLE-34

20 milimoles of acetic anhydride, 10 milimoles of isobutylbenzene and 10 ml of cyclohexane were mixed in a 50 ml of two necked round bottom flask with 0.5 gm of preactivated [400° C. in muffle furnace for 4 hrs] catalyst, Ce-Beta as prepared in Example-7. This round bottom flask was then put in an oil bath equipped with temperature controller magnetic stirrer, condenser and water circulator. The temperature of the oil bath was then slowly raised to the desired one, i.e. to 120° C. The sample were taken out periodically by means of syringe and analysed by gas chromatography using HP-5 column. The percent conversion of isobutylbenzene was nil after 5 hours as shown in table-4.

EXAMPLE-35

20 milimoles of acetic anhydride, 10 milimoles of isobutylbenzene and 10 ml of dichloroethane were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was nil after 5 hours as shown in table-4.

EXAMPLE-36

20 milimoles of acetic anhydride, 10 milimoles of isobutylbenzene and 10 ml of dichloromethane were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was nil after 5 hours as shown in table-4.

EXAMPLE-37

20 milimoles of acetic anhydride, 10 milimoles of isobutylbenzene and 10 ml of nitromethane were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 120° C. The sample were taken out periodically by means of syringe and analysed by gas chromatography using HP-5 column. The percent conversion of isobutylbenzene was nil after 5 hours as shown in table-4.

EXAMPLE-38

20 milimoles of acetic anhydride, 10 milimoles of isobutylbenzene and 10 ml of Dimethylsulfolane were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e. to 140° C. The sample were taken out periodically by means of syringe and analysed by gas chromatography using HP-5 column. The percent conversion of isobutylbenzene was 16% with 75% selectivity after 15 hours as shown in table-4.

EXAMPLE-39

20 milimoles of acetic anhydride, 10 milimoles of isobutylbenzene and 10 ml of chlorobenzene were mixed in a 50 ml of two necked round bottom flask with 0.5 gm of preactivated [400° C. in muffle furnace for 4 hrs] catalyst, Ce-Beta, as prepared in Example-7. This round bottom flask was then put in an oil bath equipped with temperature controller magnetic stirrer, condenser and water circulator. The temperature of the oil bath was then slowly raised to the desired one, i.e., to 140° C. The sample were taken out periodically by means of syringe and analysed by gas chromatography using HP-5 column. The percent conversion of isobutylbenzene was 28% with 83% selectivity after 15 hours as shown in table-4.

TABLE 1

Weight percent conversion of isobutylbenzene and selectivity towards p-acyl isobutylbenzene over different catalysts

| Ex. No. | Conversion Weight % | Selectivity % |
|---|---|---|
| 1 | 6.35 | 95 |
| 2 | 1.38 | 97 |
| 3 | NIL | NIL |
| 4 | NIL | NIL |
| 5 | NIL | NIL |
| 6 | 2.08 | 98 |
| 7 | 11.27 | 95 |
| 8 | 2 | 94 |

TABLE 2

Weight percentage conversion of isobutylbenzene and selectivity towards p-acyl isobutylbenzene over different catalysts under different catalysts

| Ex. No. | Reaction Time [Hours] | Conversion Weight % | Selectivity % |
|---|---|---|---|
| 9  | 5  | 6  | 95 |
|    | 10 | 7  | 98 |
|    | 15 | 8  | 98 |
|    | 20 | 11 | 95 |
|    | 25 | 15 | 95 |
| 10 | 5  | 8  | 11 |
|    | 10 | 9  | 97 |
|    | 15 | 10 | 97 |
|    | 20 | 13 | 95 |
|    | 25 | 21 | 89 |
| 11 | 5  | 8  | 100 |
|    | 10 | 9  | 89 |
|    | 15 | 9  | 88 |
|    | 20 | 8  | 85 |
| 12 | 10 | 9  | 97 |
|    | 15 | 10 | 97 |
|    | 20 | 13 | 95 |
| 13 | 10 | 34 | 89 |
|    | 15 | 37 | 92 |
|    | 20 | 37 | 60 |
| 14 | 10 | 13 | 81 |
|    | 15 | 14 | 75 |
|    | 20 | 17 | 72 |
| 15 | 10 | 34 | 89 |
|    | 15 | 37 | 92 |
| 16 | 10 | 14 | 78 |
|    | 15 | 13 | 85 |
| 17 | 8  | 9  | 88 |
|    | 10 | 20 | 94 |
| 18 | 8  | 10 | 94 |
|    | 10 | 19 | 88 |
| 19 | 8  | 6  | 100 |
|    | 10 | 13 | 100 |
| 20 | 8  | 27 | 87 |
|    | 10 | 34 | 90 |
| 21 | 8  | 24 | 87 |
|    | 10 | 32 | 95 |
| 22 | 10 | 87 | 87 |
|    | 15 | 37 | 81 |
|    | 10 | 37 | 87 |
|    | 15 | 36 | 81 |
|    | 10 | 26 | 98 |
|    | 15 | 23 | 89 |
|    | 10 | 14 | 94 |
|    | 15 | 9  | 95 |

TABLE 2-continued

Weight percentage conversion of isobutylbenzene and selectivity towards p-acyl isobutylbenzene over different catalysts under different catalysts

| Ex. No. | Reaction Time [Hours] | Conversion Weight % | Selectivity % |
|---|---|---|---|
|  | 10 | 3 | 96 |
|  | 15 | 6 | 98 |

TABLE 3

Weight percentage conversion of isobutylbenzene and selectivity towards p-acyl isobutylbenzene over different catalysts under different catalysts

| Ex. No. | Reaction Time [Hours] | Conversion Weight % | Selectivity % |
|---|---|---|---|
| 23 | 10 | 30 | 87 |
|  | 15 | 22 | 83 |
| 24 | 8 | 27 | 91 |
| 25 | 10 [N2 atm.] | 10 | 88 |
| 26 | 10 [Ar atm.] | 4 | 87 |
| 27 | 10 | 6 | 46 |
|  | 15 | 3 | 40 |
| 28 | 10 | 9 | 40 |
|  | 15 | 7 | 24 |

TABLE 4

Weight percentage conversion of isobutylbenzene and selectivity towards p-acyl isobutylbenzene over different catalysts under different catalysts

| Ex. No. | Solvent | Conversion Weight % | Selectivity % |
|---|---|---|---|
| 29 | Dimethylsulfolane | 20 | 82 |
| 30 | Benzonitrile | 6 | 100 |
| 31 | Nitrobenzene | 37 | 93 |
| 32 | Dichlorobenzene | 29 | 84 |
| 33 | Aceticanhydride | 7 | 24 |
| 34 | Cychlohexane | — | — |
| 35 | Dichloroethane | — | — |
| 36 | Dichloromethane | — | — |
| 37 | Nitromethane | — | — |
| 38 | Dimethylsulfolane | 16 | 75 |
| 39 | Dichlorobenzene | 28 | 83 |

What is claimed is:

1. An ecofriendly process for acylation of an alkylated benzene derivative, wherein the process has increased selectivity towards para position, and wherein the process comprises the steps of:
   (a) reacting the alkylated benzene derivative with an acylating agent in the presence of a solvent comprising a compound selected from the group consisting of nitrobenzene, dichlorobenzene, dimethylsulfolane, and benzonitrile, and a crystalline alumino silicate catalyst having general formula:

$$M_{2/n}O.Al_2O_3.x\ SiO_2.wH_2O$$

wherein M is at least one of an alkali cation, a rare earth cation, and a proton, wherein a Si/Al ratio is in the range of 5.5 to 20, wherein a weight percentage of the at least one of the alkali and lanthanide cation is in the range of 10 to 30;

wherein the step of reacting is performed at temperature in the range of 80° to 140° C. for a 5 to 25 hours;

(b) separating the solid catalyst from the reaction mixture of step (a), and
   (c) separating the acylated alkyl benzene derivative from the mixture of step (b).

2. A process as claimed in claim 1, wherein the alkylated benzene derivative is isobutylbenzene.

3. A process as claimed in claim 1, wherein the acylated alkyl benzene derivative is isobutylacetophenone.

4. A process as claimed in claim 1, wherein the acylated alkyl benzene derivative p-isobutylacetophenone.

5. A process as claimed in claim 1, wherein the crystalline alumino-silicate catalyst used is selected from the group consisting of zeolite-Y and Zeolite-β.

6. A process as claimed in claim 1, wherein the crystalline alumino-silicate catalyst is preferably modified using rare earth cations.

7. A process as claimed in claim 1, wherein the crystalline alumino-silicate catalyst is modified using lanthanum and cerium in the range of 10 to 30% by weight.

8. A process as claimed in claim 1, wherein the acylating agent is acetic anhydride.

9. A process as claimed in claim 1 wherein in step (a), the alkylated benzene derivative is are reacted with acylating agent at atmospheric conditions.

10. A process as claimed in claim 1 wherein in step (a), the alkylated benzene derivative is reacted with acylating agent at temperature in the range of 100° to 140° C.

11. A process as claimed in claim 1, wherein the solid catalyst separated in step (b) is regenerated for re-use.

12. A process as claimed in claim 1, wherein a conversion weight percent of alkylated benzene derivatives is in the range of 5 to 40%.

13. A process as claimed in claim 1, wherein the selectivity towards para position is in the range of 70 to 100%.

* * * * *